US012648816B2

(12) United States Patent
Miles et al.

(10) Patent No.: US 12,648,816 B2
(45) Date of Patent: Jun. 9, 2026

(54) COMPUTER-IMPLEMENTED METHOD FOR ESTIMATING RANGE OF MOTION OF A JOINT CONNECTING BONES

(71) Applicant: Kico Knee Innovation Company PTY. LTD, Frenchs Forest (AU)

(72) Inventors: Brad Peter Miles, Pymble (AU); Joshua Twiggs, Pymble (AU)

(73) Assignee: Kico Knee Innovation Company Pty. Ltd., Pymble (AU)

( * ) Notice: Subject to any disclaimer, the term of this patent is extended or adjusted under 35 U.S.C. 154(b) by 429 days.

(21) Appl. No.: 18/251,431

(22) PCT Filed: Nov. 2, 2021

(86) PCT No.: PCT/AU2021/051292
§ 371 (c)(1),
(2) Date: May 2, 2023

(87) PCT Pub. No.: WO2022/094656
PCT Pub. Date: May 12, 2022

(65) Prior Publication Data
US 2024/0000512 A1 Jan. 4, 2024

(30) Foreign Application Priority Data
Nov. 3, 2020 (AU) ................................ 2020904002

(51) Int. Cl.
*A61B 34/10* (2016.01)
*G06T 7/00* (2017.01)
(Continued)

(52) U.S. Cl.
CPC ............ *A61B 34/10* (2016.02); *G06T 7/0012* (2013.01); *G06T 7/251* (2017.01); *G06T 7/60* (2013.01);
(Continued)

(58) Field of Classification Search
CPC ......... G06T 7/0012; G06T 2207/30008; G06T 2210/41; G06T 17/00; G06T 2207/10081;
(Continued)

(56) References Cited

U.S. PATENT DOCUMENTS

| | | | |
|---|---|---|---|
| 2013/0211531 A1* | 8/2013 | Steines | .................. A61F 2/3859 |
| | | | 623/20.14 |
| 2015/0088145 A1* | 3/2015 | McCarthy | .............. A61B 34/20 |
| | | | 606/91 |

(Continued)

FOREIGN PATENT DOCUMENTS

| | | | | |
|---|---|---|---|---|
| CN | 110348321 A | * | 10/2019 | ............. G06N 3/049 |

OTHER PUBLICATIONS

Arbabi et al., A Fast Method for Finding Range of Motion in the Human Joints, Proceedings of the 29th Annual International Conference of the IEEE EMBS, Aug. 23-26, 2007, pp. 5079-5082, doi: 10.1109/IEMBS.2007.4353482. PMID: 18003148.*

(Continued)

*Primary Examiner* — Guillermo M Rivera-Martinez
(74) *Attorney, Agent, or Firm* — Nixon Peabody LLP

(57) ABSTRACT

A system and method (100) for estimating range of motion of a joint (3) connecting a first bone (5) to a second bone (7), the joint comprising a point of rotation (9) defining rotation of the first bone relative to the second bone. The method comprises: obtaining (110) a digital model of the joint that includes, for each bone (5, 7), respective mesh models with sets of mesh points that represent the bone; determining (120) polar coordinates for the set of mesh points, with the point of rotation (9) as a pole (21) of the polar coordinates; and calculating (130), based on the polar coordinates, multiple angular distance values relating to rotation of the joint, where the multiple angular distance values are indicative of an angular distance between points in the set of mesh points, (Continued)

Obtain a digital model of the joint, the digital model comprising: a first mesh model of the first bone that includes first mesh points; and second mesh model of the second bone that includes second mesh points — 110

Determine polar coordinates for the first set of mesh points and the second set of mesh points, where the point of rotation of the joint is the pole of the polar coordinates — 120

Calculate multiple angular distance values relating to rotation of the joint, where each of the multiple angular distance values are indicative of an angular distance between one point in the first set and one point in the second set of mesh points, and where the angular distance being indicative of the range of motion of the joint — 130

Generate a visualisation of the digital model, wherein the visual appearance of the first set of mesh points and the second set of mesh points is indicative of the angular distance value — 160

Receive an update of the digital model of the implant — 170

Recalculate the multiple angular distance values based on the update — 180

100 and the angular distance being indicative of the range of motion of the joint.

18 Claims, 9 Drawing Sheets

(51) Int. Cl.
*G06T 7/246* (2017.01)
*G06T 7/60* (2017.01)
*G06T 17/20* (2006.01)
*G06T 19/20* (2011.01)

(52) U.S. Cl.
CPC ............. *G06T 17/20* (2013.01); *G06T 19/20* (2013.01); *A61B 2034/104* (2016.02); *A61B 2034/105* (2016.02); *A61B 2034/107* (2016.02); *G06T 2207/10028* (2013.01); *G06T 2207/30008* (2013.01); *G06T 2207/30052* (2013.01); *G06T 2210/41* (2013.01); *G06T 2210/56* (2013.01); *G06T 2219/2012* (2013.01)

(58) Field of Classification Search
CPC . G06T 2207/10088; G06T 2207/30004; G06T 2207/10116; G06T 2207/20044
See application file for complete search history.

(56) References Cited

U.S. PATENT DOCUMENTS

| 2015/0193591 | A1* | 7/2015 | Lavallee | A61B 34/10 |
| | | | | 703/1 |
| 2016/0220312 | A1* | 8/2016 | Mahfouz | G16H 20/40 |
| 2017/0128135 | A1 | 5/2017 | Mccarthy et al. | |
| 2017/0178413 | A1 | 6/2017 | Gotte et al. | |
| 2017/0372472 | A1* | 12/2017 | Takahashi | A61B 6/505 |
| 2019/0239926 | A1* | 8/2019 | Pavlovskaia | A61B 17/1703 |
| 2019/0380792 | A1* | 12/2019 | Poltaretskyi | G06F 3/0482 |
| 2019/0388123 | A1* | 12/2019 | Pavlovskaia | G06T 19/00 |
| 2021/0012492 | A1* | 1/2021 | Karade | G06T 7/30 |
| 2021/0121244 | A1* | 4/2021 | Innanje | A61B 34/10 |
| 2021/0192759 | A1* | 6/2021 | Lang | A61B 34/10 |

OTHER PUBLICATIONS

"International Application No. PCT/AU2021/051292", International Search Report and Written Opinion, mailed Dec. 14, 2021, 13 pages.

Arbabi, "Contact Modeling and Collision Detection in Human Joints", Thesis, (2009), Abstract, retrieved from https://doi.org/10.5075/epfl-thesis-4421, 121 pages.

* cited by examiner

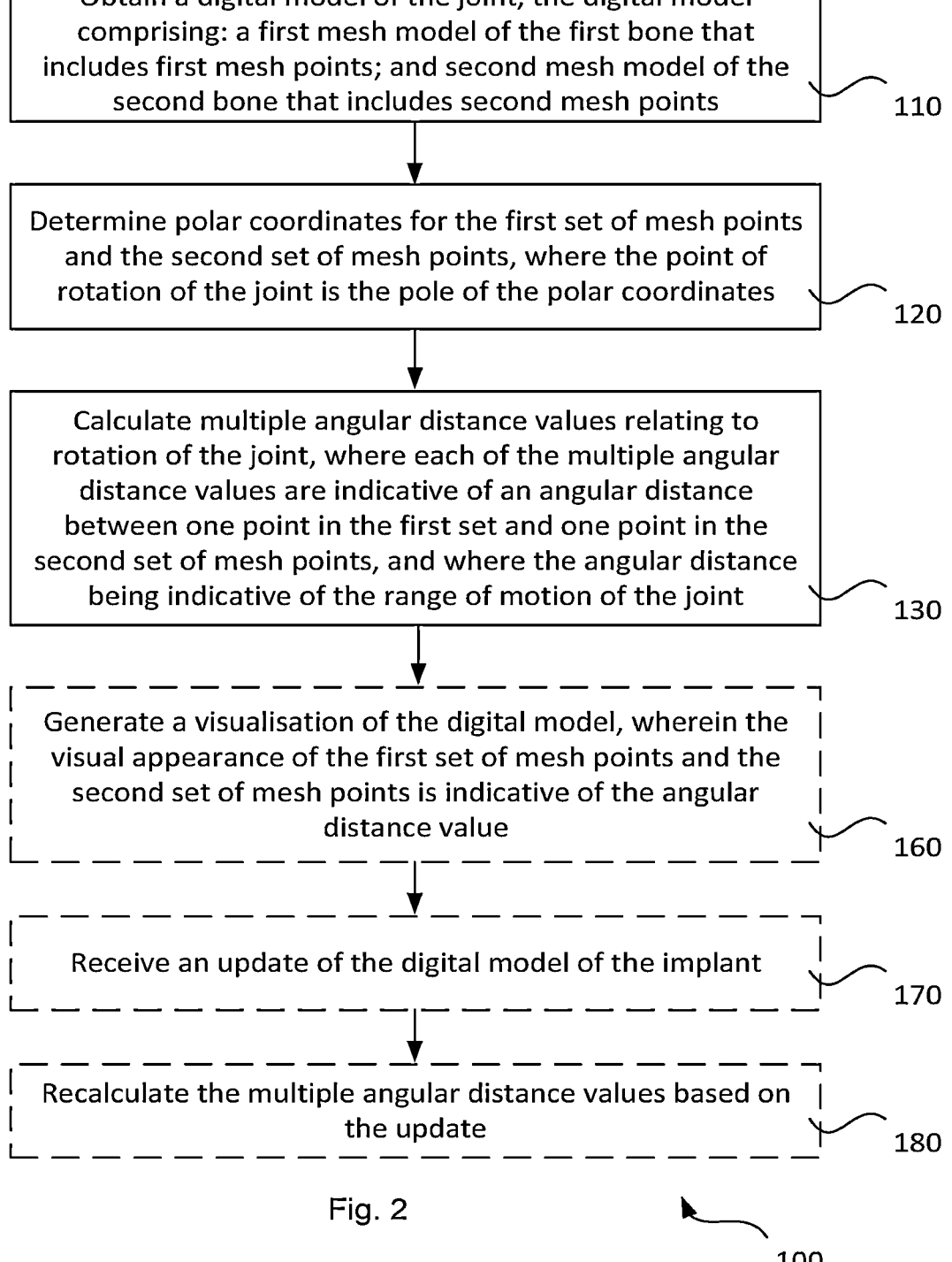

Obtain a digital model of the joint, the digital model comprising: a first mesh model of the first bone that includes first mesh points; and second mesh model of the second bone that includes second mesh points

110

Determine polar coordinates for the first set of mesh points and the second set of mesh points, where the point of rotation of the joint is the pole of the polar coordinates

120

Calculate multiple angular distance values relating to rotation of the joint, where each of the multiple angular distance values are indicative of an angular distance between one point in the first set and one point in the second set of mesh points, and where the angular distance being indicative of the range of motion of the joint

130

Generate a visualisation of the digital model, wherein the visual appearance of the first set of mesh points and the second set of mesh points is indicative of the angular distance value

160

Receive an update of the digital model of the implant

170

Recalculate the multiple angular distance values based on the update

72
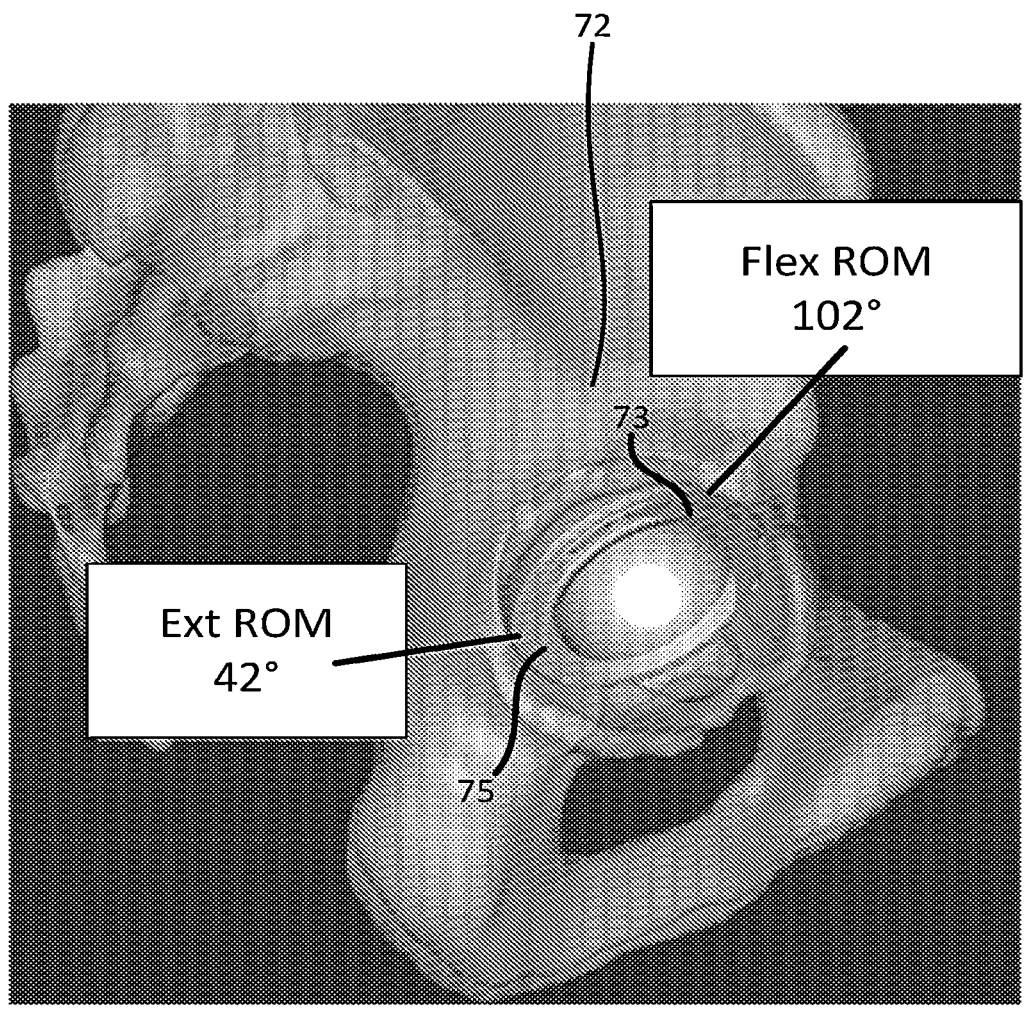
Flex ROM
102°
73
Ext ROM
42°
75
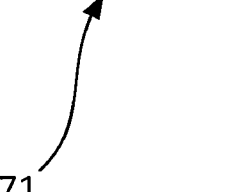
71
Fig. 7

COMPUTER-IMPLEMENTED METHOD FOR ESTIMATING RANGE OF MOTION OF A JOINT CONNECTING BONES

TECHNICAL FIELD

This disclosure relates to estimating range of motion of a joint in the body.

BACKGROUND

Range of motion (ROM) is an important metric for joint functioning. In particular, during joint surgeries, such as total hip replacements, the final success of the surgery depends on the achieved ROM after replacement. However, a small change in the positioning of the implant can have a large effect on the resulting ROM. In addition, the parts of the joint which limits the ROM, that is, the point where the two bones touch at maximum rotation can change after the position of the implant is changed minimally. These factors make it difficult to place the implant and conduct the surgery optimally to achieve maximum ROM.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

A computer-implemented method for estimating range of motion of a joint connecting a first bone to a second bone, the joint comprising a point of rotation defining rotation of the first bone relative to the second bone about the point of rotation. The method includes the step of: obtaining a digital model of the joint, the digital model comprising: a first mesh model representing the first bone and comprising a first set of mesh points; and a second mesh model representing the second bone and comprising a second set of mesh points. The method further includes determining polar coordinates for at least one of the first set of mesh points and the second set of mesh points, with the point of rotation as a pole of the polar coordinates. The method also includes calculating, based on the polar coordinates, multiple angular distance values relating to rotation of the joint, each of the multiple angular distance values being indicative of an angular distance between one point in the first set and one point in the second set, and the angular distance being indicative of the range of motion of the joint.

The range of motion of the joint may be determined by the angular distance where the points from the first set and second set are calculated to contact.

In some examples, the method includes calculating the multiple angular distance values comprises selecting for a point in the first set, a point in the second set that is the nearest neighbour of the point in the first set based on the polar coordinates.

In some examples, the method comprises performing a nearest neighbour search. The nearest neighbour search may be based on a space-partitioning data structure. In some examples the space-partitioning data structure comprises a k-d tree.

In some examples, the method comprises determining an angular distance value for multiple points on opposing surfaces of the first bone and the second bone.

In some examples, the angular distance value is a difference in an angle between the first set of mesh points and the second set of mesh points.

In some examples, the polar coordinates are two-dimensional comprising one distance value and one angle value.

In some examples, the polar coordinates are supplemented with an azimuthal angle to define spherical coordinates in three-dimensional space.

The method may further comprise generating a visualisation of the digital model, wherein a visual appearance of the first set of mesh points and the second set of mesh points is indicative of the angular distance value. In some examples, the visual appearance is a colour value. In some further examples, the colour value(s) represents attainment, or failure to attain, a specified anatomic range of motion value.

In some examples, the digital model of the joint comprises a digital model of an implant that replaces a part of at least one of the first bone, the second bone, or another implant and defines the rotation of the first bone relative to the second bone. In some examples the another implant is an existing implant in the patient. In other examples, the another implant is an alternative option of an implant that was under consideration.

In some examples, the method further comprises: receiving an update on the digital model of the implant; and re-calculating the multiple angular distance values based on the update.

In some examples, the update comprises position information of the implant. In further examples, the update comprises a cut angle of the first bone or the second bone.

In some examples of the method, at least one of the first mesh model and the second mesh model is a triangular mesh model defined by multiple triangles approximating a surface of the respective first bone and second bone.

In further examples, at least one of the first set of mesh points and the second set of mesh points comprise one or more of: vertices of the triangles, and centroids of the triangles.

There is also disclosed software that, when executed by a computer, causes the computer to perform the method described herein.

There is also disclosed a computer system for estimating range of motion of a joint connecting a first bone to a second bone, the joint comprising a point of rotation defining rotation of the first bone relative to the second bone about the point of rotation, wherein the computer system comprises at least one processor configured to: obtain a digital model of the joint, the digital model comprising: a first mesh model representing the first bone and comprising a first set of mesh points; and a second mesh model representing the second bone and comprising a second set of mesh points; determine polar coordinates for at least one of the first set of mesh points and the second set of mesh points, with the point of rotation as a pole of the polar coordinates; and calculate, based on the polar coordinates, multiple angular distance values relating to rotation of the joint, each of the multiple angular distance values being indicative of an angular distance between one point in the first set and one point in the second set, and the angular distance being indicative of the range of motion of the joint.

In some examples of the computer system, the at least one processor is configured to: select, for a point in the first set, a point in the second set that is the nearest neighbour of the point in the first set based on the polar coordinates.

In some examples of the computer system, the at least one processor is configured to: receive an update on the digital model of the implant; and re-calculating the multiple angular distance values based on the update.

BRIEF DESCRIPTION OF DRAWINGS

FIG. 2 is a flow diagram of a method for estimating range of motion of the joint;

FIG. 7 is a three-dimensional visualisation of the acetabulum with a visual overlay;

DESCRIPTION OF EMBODIMENTS

Overview

Figure 1:
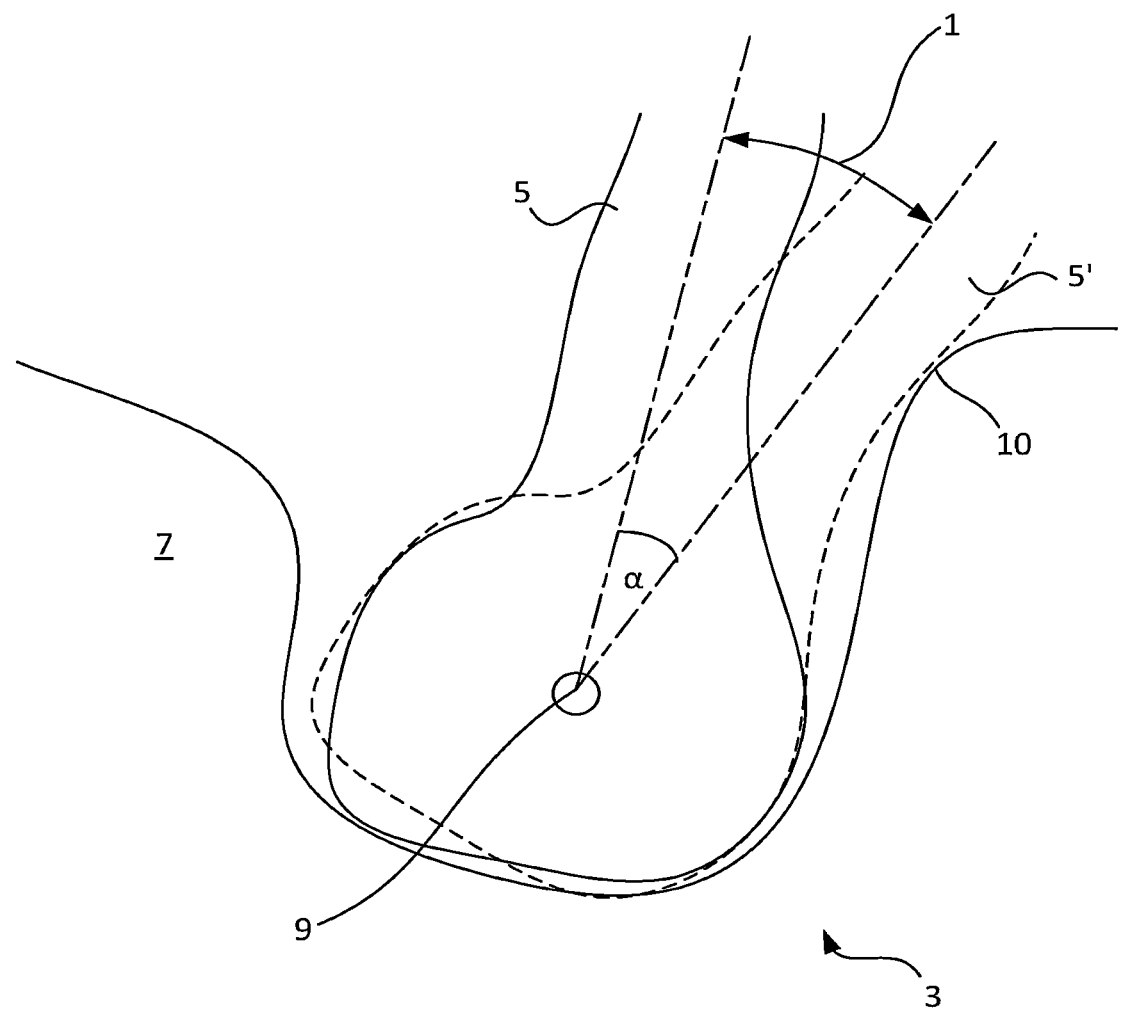
FIG. 1 illustrates a joint where a first bone is movable relative to a second bone, where the first bone is shown in two positions.

FIG. 1 illustrates a joint 3 that includes a first bone 5 and a second bone 7. The first bone 5 in solid outline illustrates the first bone at a first position. The first bone can rotate in the joint 3 about a point of rotation 9 relative to the second bone. FIG. 1 also illustrated the first bone (designated by 5' and in broken lines) at a second position where the first bone is at the limit of rotation. In particular, the first bone is at a maximum incidence where part of the first bone 5 is in contact 10, or near contact, with the second bone 9 to prevent further rotation.

Figure 3:
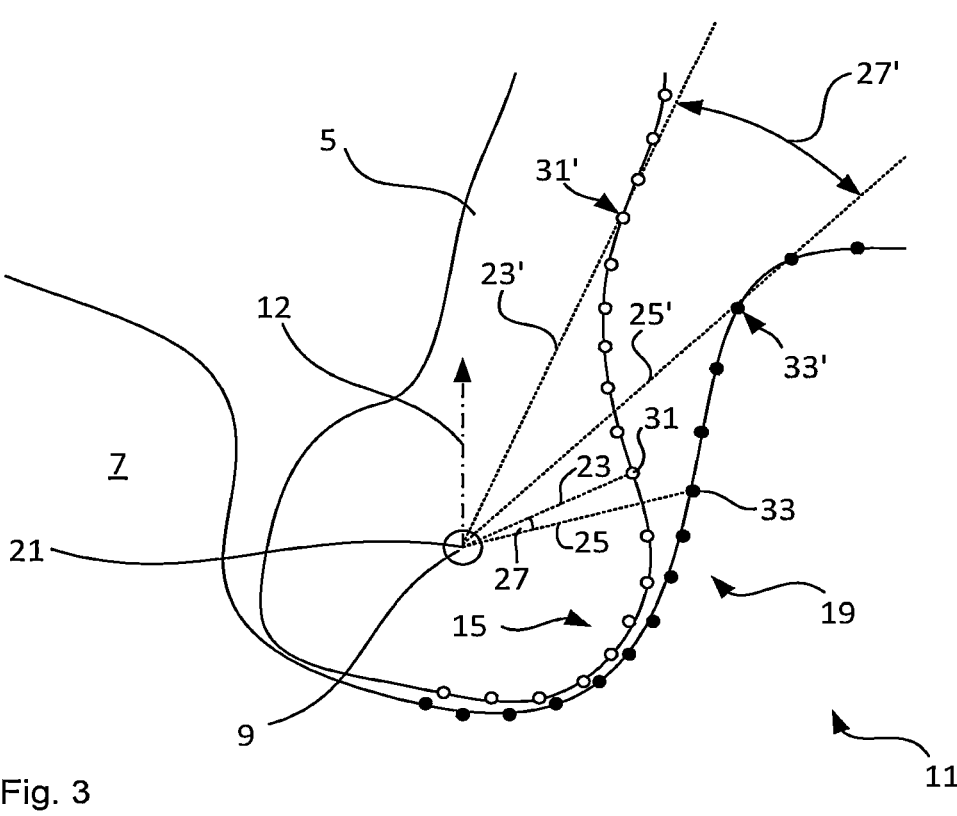
FIG. 3 illustrates a digital model of the joint in FIG. 1 at the first position, where the bones are represented with sets of mesh points.

The disclosed method 100 is directed to estimating range of motion 1 of the joint 3 connecting the first and second bone 5, 7. This method includes obtaining 110 a digital model 11 of the first and second bones 5, 7 as respective first mesh models 13 and second mesh model 17. The mesh models includes respective first and second set of mesh points 15, 19 that correspond to the surfaces of the bones 5, 7 as illustrated in FIG. 3.

The method includes determining 120 polar coordinates 23, 25 for the first set of mesh points 15 and second set of mesh points 19, with the point of rotation 9 of the joint as the pole 21 of the polar coordinates 23, 25. The polar coordinates 23, 25 are represented as lines in the Figures, but it is to be appreciated this line represents a distance from the pole and an angle from a reference direction 12.

The method further includes calculating 130, based on the polar coordinates (23, 25), multiple angular distance values 27 relating to the rotation of the bones in the joint 3. In particular, each of the multiple angular distance values 27 are indicative of an angular distance 27 between one point 31 in the first set 15 and one point 33 in the second set 17. The angular distance 30, that shows the amount or rotation possible for corresponding point pairs, are indicative of range of motion 1 of the joint.

Figure 4:
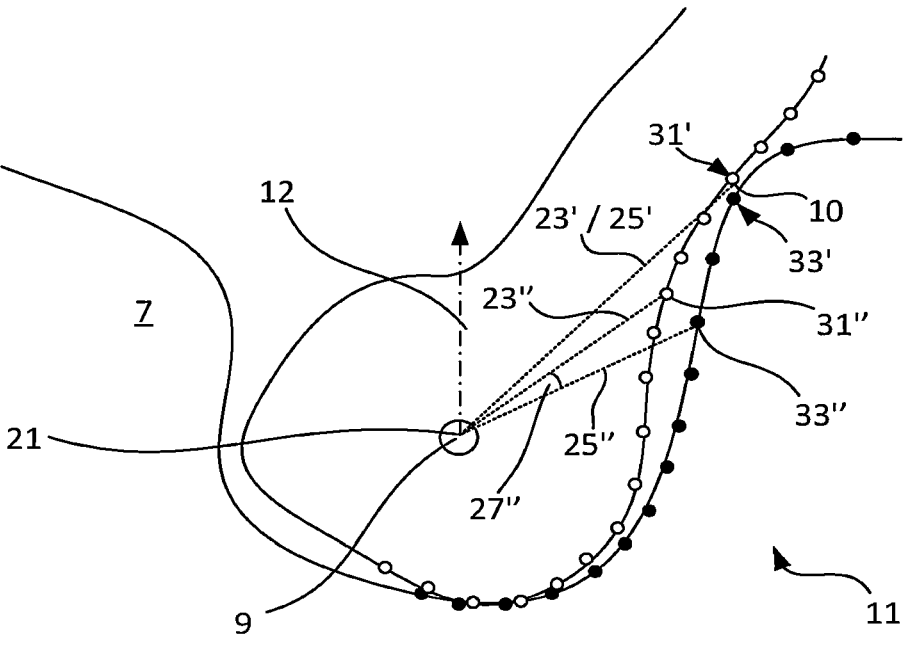
FIG. 4 illustrates a digital model of the joint in FIG. 3 at the second position where the first bone impinges the second bone at the end of the range of motion.

In some examples, this includes calculating the smallest angular distance 30 between the point 31', 33' pairs as best illustrated in FIG. 4. This indicative of the joint 3 rotating to maximum range of motion 3. (i.e. the points as being indicative of the maximum range of motion 1.

It is an advantage that the polar coordinates are used because they enable explicit calculation of the angular distance values. Therefore, it is not necessary to gradually rotate the mesh points (such as in Cartesian form) until contact occurs. Therefore, the method is computationally more efficient. Further, angular distance values can be calculated for many points, which can indicate to the surgeon which areas (or series of points) that limit the range motion. For example, this can highlight the presence of osteophytes, which could be removed to extend the range of motion relatively easily.

The steps of a specific example of the method 100 will now be described in detail.

Obtaining the Digital Model 110

The digital model 11 of the patient's joint 3 can be based on data from medical imaging data, such as CT (X-ray computed tomography), magnetic resonance imaging (MRI), etc. These images may be analysed by a computer to generate a digital model, that can include 3D models such as a mesh model to represent the bones 5, 7 of the joint. In some examples the digital models may incorporate, in part, information and models of ideal bones to complete data missing from the medical images.

The digital model importantly models the surfaces of the bones 5, 7 that may contact each other during movement. Such contact will define the limits of the range of motion 1 for that joint 3. To that end, the digital model includes a first mesh model 13 that represents the first bone 5 and a second mesh model 17 that represents the second bone 7. The mesh models may include triangular mesh models that is defined by multiple triangles that approximate the respective surfaces of the first and second bones 5, 7.

In turn the mesh models 13, 17 also comprise sets of mesh points that correspond to discrete points on the modelled surface of the bone. In some examples, these mess points 15, 19 are based on the vertices of the triangles of the triangular mesh model. In other examples, the mesh points 15, 19 are centroids of the triangles of the triangular mesh model.

The initial digital model may initially include various forms of 2D images, 3D models, etc., and based on various coordinate systems, and with different frames of references. To simplify further computation, the data is converted to polar coordinates.

Determining Polar Coordinates 120

FIGS. 3 and 4 illustrate a cross-section of the joint 3 with the surface of the bones 5, 7 as continuous lines. At least part of the first mesh points 15 are shown as hollow circles 31 and at least part of the second mesh points 15, 19 are shown as solid circles 33.

The method includes determining 120 polar coordinates (23, 25) for the points making up the mesh points. As illustrated in FIG. 3, the polar coordinates (23, 25) are based from a pole 21 that also coincides with the point of rotation 9 of the joint 3.

In the example of FIG. 3, the analysis is two-dimensional where each polar coordinate includes one distance value and one angle value. This simplified form aids further calculation as the main focus for range of motion is angular values.

Calculating Multiple Angular Distance Values 130

With polar coordinates 23, 25 for mesh points 15, 19 the method includes determining 130 multiple angular distance values 27 relating to rotation 9 of the joint 3. Each of the multiple angular distance values 27 are indicative of an angular distance 27 between one point 31 in the first set 15 and another point 33 in the second set 19 of mesh values. Typically, the point 31 and other point 33 are on opposing surfaces of the first bone 5 and second bone 7.

Referring to FIGS. 3 and 4, we will now look at one specific angular distance value 27'. This angular distance value 27' is calculated from one point 31' of the first bone 5 and another point 33' of the second bone 7, which may include the difference in the polar angle of those points. As shown in FIG. 4, when point 31' and 33' are close, or intersect, this represents one end of the range of motion for that joint 3. Since the points 31', 33' are defined by polar coordinates, calculation of this end of the range of motion can be simplified to determining where the angle values for the points 31', 33' are equal (or close to equal).

Such determinations are done multiple times for multiple corresponding pairs of points 31, 33 between the first and second bone 5, 7. Referring to FIGS. 1 and 4, it is clear that the first bone 5 can rotate from the first position by angle α the until point 31' impinges 10 with point 33' (where the respective polar angle values are approximately equal). At the same angle of rotation, further points 31" on the first bone 5 and opposing point 33" on the second bone 7 are still spaced apart and will have different polar angle values. Thus in some examples, determining an extreme of range of motion 1 of the first bone 5 to the second bone 7 can simply include identifying the first pair of points 31, 33 that will impinge by having polar angle values that are the same (or substantially the same) when the joint 3 is rotated.

FIGS. 3 and 4 illustrate determination of one end of the range of motion 1 of the joint 1 and it is to be appreciated that for the opposite end of the range of motion 1, similar determinations can be made to identify points where the polar angle values coincide (or nearly coincide).

Although FIGS. 3 and 4 illustrate the determination on a particular two dimensional plane, it is to be appreciated that the computer-implemented method could repeat these calculation at additional two-dimensional planes with rotation around a different axes through the point of rotation 9. For example, a two-dimensional plane that is perpendicular to the plane illustrated in FIGS. 3 and 4.

In yet further examples, the method may be extended to points with polar coordinates in three dimensions. In some examples, this includes supplementing the polar coordinates with an azimuthal angle to define spherical coordinates in three-dimensional space (e.g. radial distance, polar angle, and azimuthal angle). Similar to the above, this can include determining the relative movement of bones 5, 7 and the resultant angular distance values between points that will indicate the range of motion. This can include determining ranges of motion around a single point of rotation (but around different axes of rotation).

Selecting Nearest Neighbour

In calculating 130 the multiple angular distance values, the method 100 may include selecting for a point 31 in the first set of mesh points 15, a point 33 in the second set of mesh point 17 that is the nearest neighbour to each other based on the polar coordinates. In some examples, this is useful in that selection of the closest neighbour may reduce the number of calculations of the multiple angular distances as points 31, 33 that are substantially spaced apart will unlikely to impinge and be the limiting factor of the range of motion 1. As an example, with reference to FIG. 4, the method may wish to skip calculations between point 31' of the first bone 5 and point 33" of the second bone 7 as the joint will unlikely to be rotated so that points will contact.

In some examples, the nearest neighbour search may be an exact nearest neighbour search. In other examples, an approximate nearest neighbour search algorithm may be used for computational efficiency. Such nearest neighbour search may include using data structures and algorithms in the ANN library (www.cs.umd.edu).

In some examples, the method includes performing a nearest neighbour search between points in the first set of mesh points 15 and points in the second set of mesh points 19. This can include identifying specific corresponding pairs between the sets 15, 19. It is to be appreciated that in some examples, the number of points in the sets are not direct one for one matches. In some examples, the method may include upscaling and/or downscaling the number of points in the sets to allow pairs of points to be matched with a nearest neighbour. In some example, this may include using interpolation to provide additional points for the mesh points, or reducing the number of points in the mesh with interpolation. It is to be appreciated that various nearest neighbour search method can be used, including both exact and approximation methods. These can include: linear search, space-partitioning.

In some examples, the nearest neighbour search is based on a space-partitioning process and where the digital model is stored, at least in part, in a space-partitioning data structure. In further examples, the space-partitioning data structure comprises a k-d tree.

In some examples, the nearest neighbour search can be done before the step of calculating the multiple angular distance values to reduce computation of data at the computer.

An example of determining the nearest neighbour for a specific angle of motion after conversion to polar coordinates can include:

Angle 1 (modelled angle to contact)
Distance 1 (distance to a point in the first set)
Distance 2 (distance to a point in the second set)

In this example of calculation, the common angle to contact (Angle 1) is used and therefore the nearest neighbour solution is calculated based on the difference between Distance 1 and Distance 2. That is, the nearest neighbour calculation does not require the specific angle of motion under evaluation which can reduce the computational burden.

In another examples, determining the nearest neighbour after conversion to polar coordinates can include:

Angle 1 (angle to contact)
Angle 2 (circumferential about the pole of motion for a point)
Distance 1 (distance to a point from the pole).

Distance 1 and Angle 2 are used to run the nearest neighbour calculation for a point (where the point calculation can be run separately for the first set and the second set).

In this example, every angle of motion possible for Angle 1 can be checked for every angle of Angle 2.

Visualisation of the Digital Model

Figure 5:
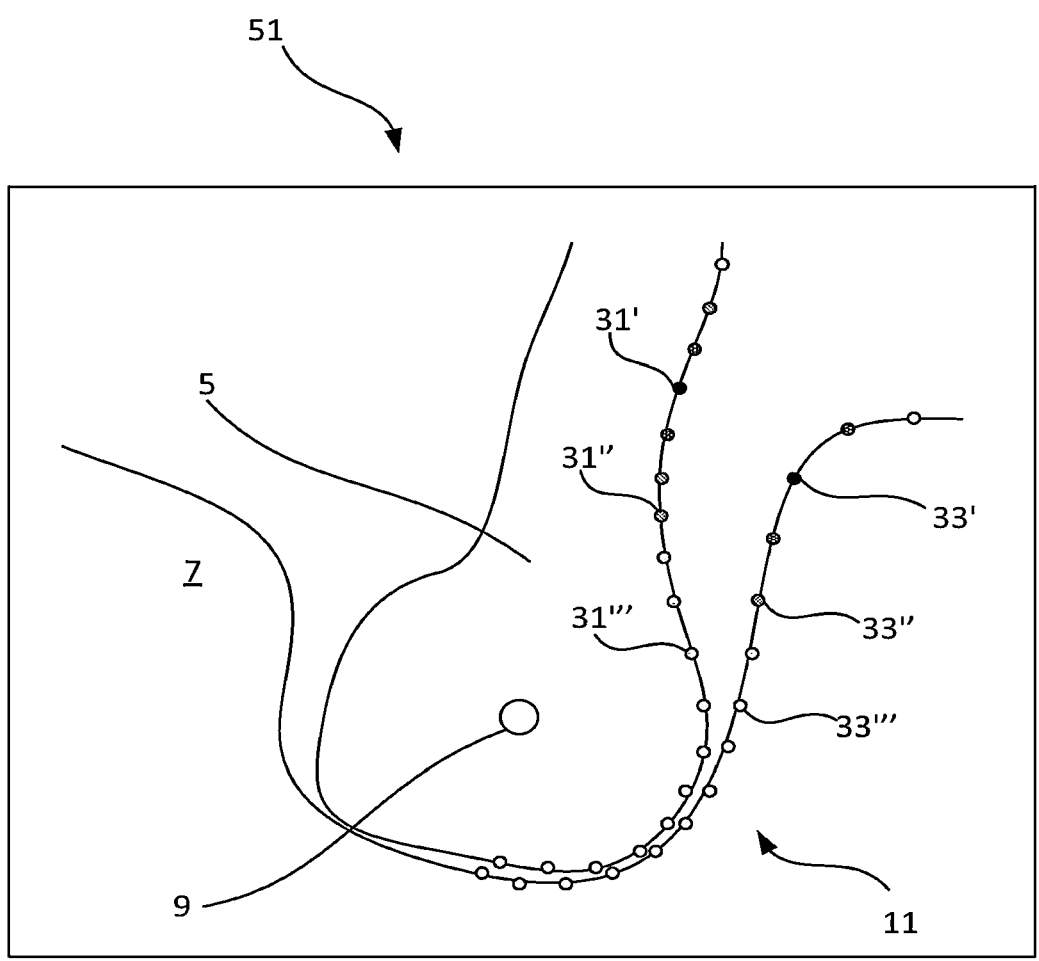
FIG. 5 is a visualisation of the digital model wherein the visual appearance of the mesh points is indicative of respective angular distance values that are in turn indicative of the range of motion of the joint.

FIG. 5 shows an example visualisation 51 of the digital model generated 160 from the method. The visualisation 51 alters the visual appearance of the first and second set of mesh points 15, 19 to indicate results of the calculated multiple angular distance values.

Points 31' and 33' (having the visual appearance of a solid circle) corresponds to the portions of the surfaces of the bones 5, 7 that impinge and limit of the range of motion (see FIG. 4). That is, points 31' and 33" are coloured black (or other specified colour) to show that they are points that have the minimum angular distance (and likely to contact) at the end of the range of motion.

Points 31" and 33" are in grey to show that these points have angular distance values that are close, but not the closest compared to other points. This may be useful to the surgeon for secondary consideration. For example, if the surgeon removes bone from points 31' and 33', then the grey points 31" and 33" would likely correspond to the surfaces that limit the range of motion.

Finally, points that have the largest corresponding angular distance values are hollow circles (or coloured white, or another specified colour) to show these points on the corresponding surfaces of the bone are unlikely to be the portions of the surface that limit the range of motion.

Thus the visual appearance allows users, such as surgeons, to easily identify the points or areas that limit the range of motion for the joint. This will assist operation planning, such as identifying areas of concern and for surgical intervention. This can also assist in providing an indication of the outcome of surgical procedures. This can include identifying osteophytes and estimating a new range of motion with surgery to remove the osteophytes. This can be done by removing the points of osteophytes from the digital model and recalculating the multiple angular distances.

In some examples, the visual appearance is a colour value, such as different colours to indicate the proximity of the points 31, 33. Alternatively, the method may calculate to show with the colour value whether the point 31, 33 attains of fails to attain the specified anatomic range of motion. That it, the user may input a desired anatomic range of motion, and the colours are indicative of whether the joint can achieve that range or motion or alternatively indicate specific points on the bone that prevent that desired range of motion.

It is to be appreciated that the visual appearances can be in other forms, such as colouring of the outline near the points, or an area proximate to those points. In other examples, the visual appearance may include shading, colour scales, highlighting or patterns. In yet further examples, the visual appearance may include other visual indicia such as arrows, circling of points 31, 33, or other visually distinctive markers near the points that limit the range of movement.

FIG. 7 illustrates an example of a three-dimensional visualisation 71 of the acetabulum 72 where the visual appearance of mesh points is provided as an overlay. In particular the overlay shows an area associated with the subset of mesh points instead of a number of discrete coloured points. In this example, a first area 73 of the joint is marked with a coloured overlay with a colour (e.g. red). Firstly, this indicates the region of bone that limits motion. Secondly, the colour indicates that the current structure fails to attain the desired range of motion. This example also shows a second area 75 of the joint that is marked with a different colour overlay (e.g. green). In this example, the different colour (green) indicates that the part that limit the range of motion allows attainment of the desired range of motion. Therefore the surgeon can be prompted to focus on the first area 73 in red for further planning or operation to achieve the desired effects.

Figures 8, 9:
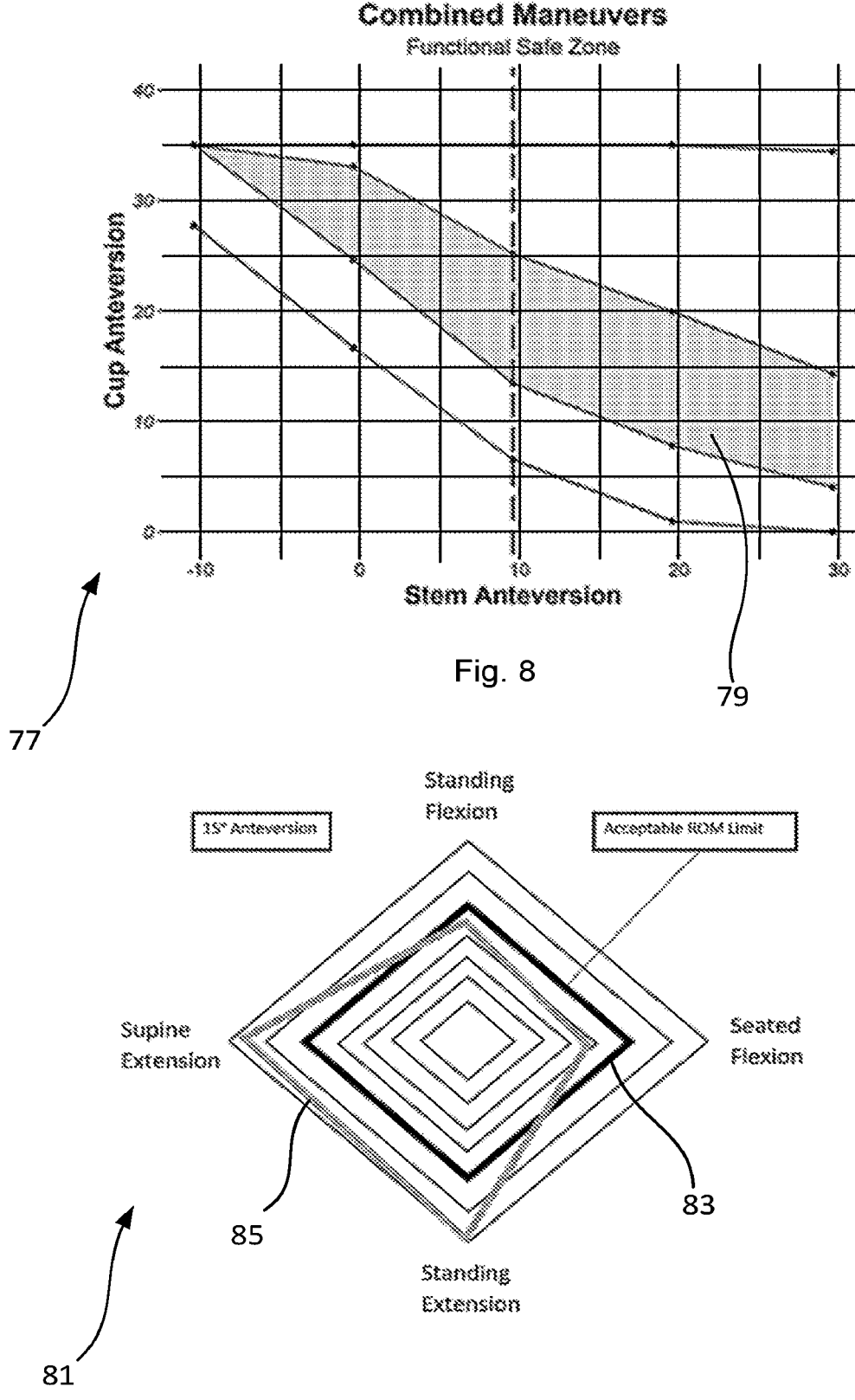
FIG. 8 is a graph showing the result of range of motion calculation for various configurations of components of a joint.
FIG. 9 is a graphical representation of range of motion requirements, the acceptable range of motion, and the calculated range of motion for a configuration.

FIG. 8 illustrates a graph illustrating the results of the calculated range of motion for various configurations of the joint. This can includes showing portions where the desired range(s) of motion is achieved. For example, the area 79 shown in green, represents an area where the configurations of the joint (in this case anteversion of the stem and cup) safely achieves the desired range of motion. This aids the surgeon to select configuration that comfortably fit in safe zones and assess the margins for error for surgery. For example, selecting cup anteversion of twenty and stem anteversion of ten sits in the middle of a safe zone so that small deviations from those values will still achieve the desired range of motion.

FIG. 9 illustrates a graphical representation 81 noting four important range of motion requirements. Namely, standing flexion, standing extension, supine extension, seated flexion. In FIG. 9, the acceptable range of motion 83 is graphically shown as a square, with the corners at the four parameters. For the selected configuration, the calculated range of motion 85 is shown as a four sided polygon. In this particular example, it is clear that the range of motion for the configuration satisfies the supine extension and standing extension requirements. However, this falls short of the acceptable range of motion 83 for standing flexion and seated flexion. This result is shown by having the four sided polygon 85 having corners that fall short of the graphical boundaries of the square 83 as well as a colour (such as red) denoting failure to attain the desired range of motion.

Visualisation of the Digital Model an Implant

Figure 6:
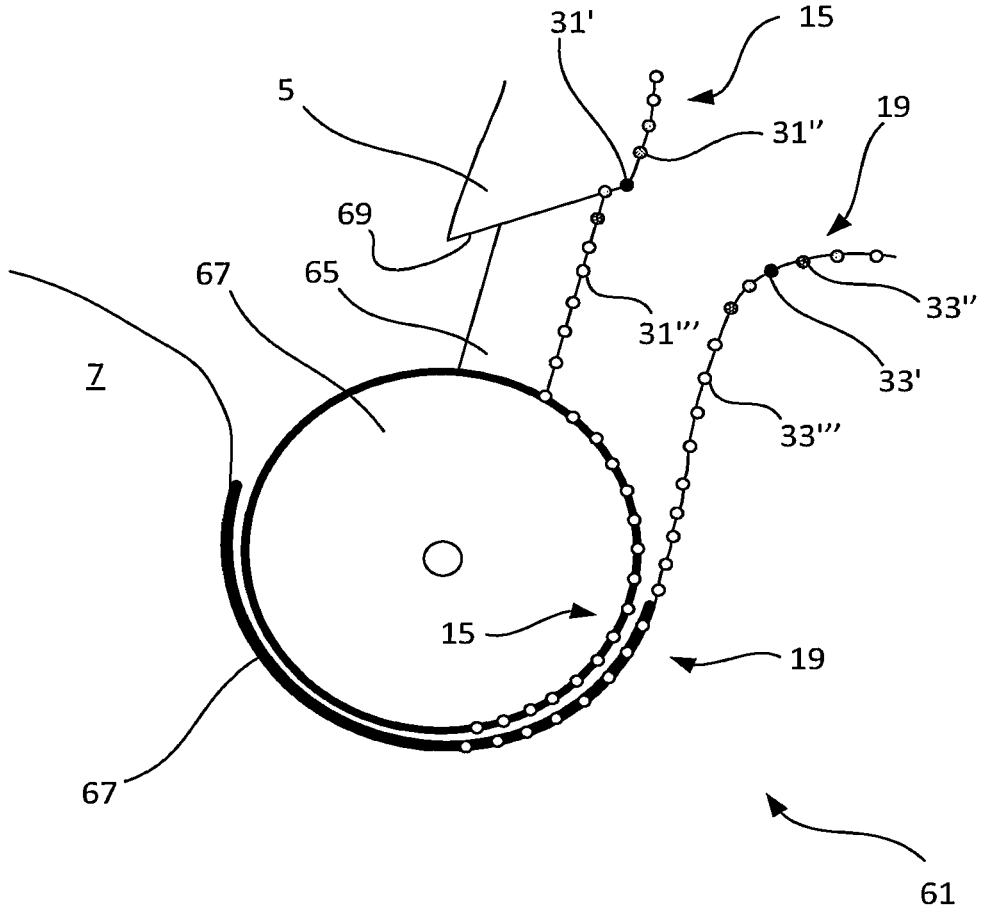
FIG. 6 illustrates a digital model of a joint where an implant replaces at least part of the first bone and second bone.

FIG. 6 illustrates a digital model 61 of a joint 63 that further comprises an implant 65, 66, 67 that replaces at least part of the bone of a natural joint. In this example, the implant 65 replaces at least parts of both the first bone 5 and the second bone 7. In particular replacing the femoral head of the first bone and the acetabulum of the second bone during a hip replacement surgery.

The implant includes a stem 65 and head 66 that replaces part of the first bone 5. The implant also includes a cup 67 that replaces part of the second bone 7. Such implants form a hip prosthesis for a hip replacement.

The digital model 61 may be used as a tool to predict and analyse the results of a proposed implant. This can include comparing the range of motion with an implant compared to before the surgery (such as comparing with the digital models 11 in FIGS. 3 to 5). The digital model 61 may also be used as a tool for the surgeon to consider how to operate and cut the bone 5, 7.

In this digital model, the first mesh model 13 representing the first bone 5 with mesh points 15 include parts of the implant, in particular the stem 65 and head 66, that will be attached to the first bone 5. Similarly, the second mesh model 17 include parts of the cup implant 67 as the cup forms part of the relevant surface of the joint 61.

Referring to FIG. 2, when considering the effect of an implant on an existing joint 3, the method includes receiving 170 an update of the digital model 61 of the implant 65, 66, 67. This can include combining parts of the existing digital model 11 of the bones of the patient, with model data of the implant components.

This may include updating the model of the bones 5, 7 of the patient to take into account one or more cuts 69 to the bone. In some examples, this may include providing a cut angle.

The method 100 may also include updating the digital model by providing position information of the implants 65, 66, 67 relative to the corresponding bones 5, 7.

Once the digital model 61 is updated with information to take into account the proposed surgical procedures and implants, the method includes re-calculating 180 the multiple angular distance values based on the update digital model 61.

Referring back to FIG. 6, the mesh points indicate significant points 31', 33' (which are solid black circles to indicate they will be the points likely to contact 10 at end of the range of motion), have moved compared to the digital model 11 in FIG. 5. This is because the surface contours have changed due to the surgical cuts and implants.

In addition to estimating the resultant range of motion, the visualisation of the updated digital model 61 may be used by the surgeon to identify issues with the proposed procedure ahead of surgery. For example, the surgeon may identify that point 31' is likely to be a contact point, and due to the cut it is also a relatively sharp and fragile part of the first bone 5. To avoid issues with that point 31' fragmenting or gouging the second bone 7, the surgeon may elect to remove the edge at 31' and profile the first bone 5 so that there is a wider and even contact surface with the second bone.

Figure 10:
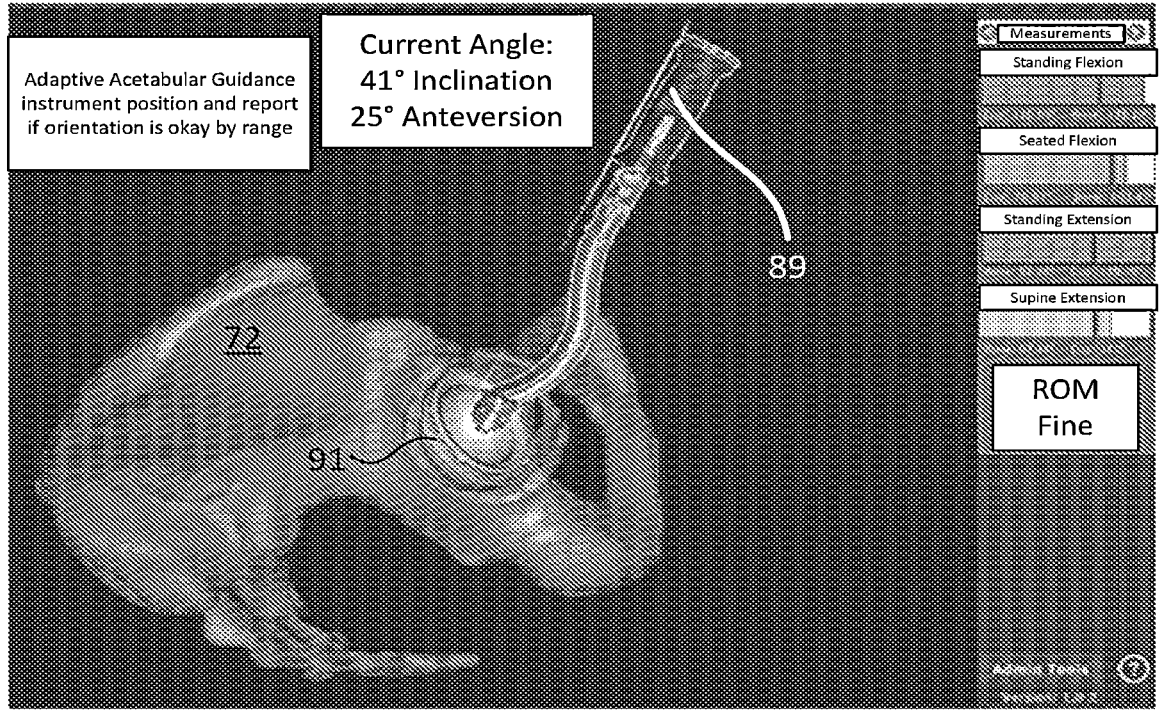
FIG. 10 is a three-dimensional visualisation of an acetabulum and live tracking of a surgical instrument placing an implant.

FIG. 10 illustrates an example of a three-dimensional visualisation 87 of the acetabulum 72 with live tracking of a surgical instrument 89 placing an implant 91 (such as a cup implant). This can show the relative position and orientation of the components to aid the surgeon. The colour (or colour overlay) of the acetabulum, or other visual indicia, can indicate when the implant 91 is configured with the acetabulum so that that the implant can achieve the desired range of motion.

Processing Device

Figure 11:
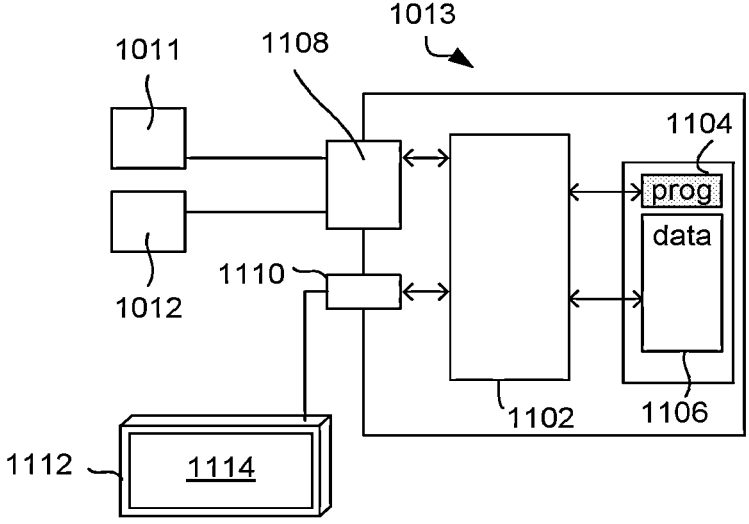
FIG. 11 illustrates a schematic of a processing device.

The processing device 1013, as illustrated in FIG. 11, includes a processor 1102 connected to a program memory 1104, a data memory 1106, a communication port 1108 and a user port 1110. The program memory 1104 is a non-transitory computer readable medium, such as a hard drive, a solid state disk or CD-ROM. Software, that is, an executable program stored on program memory 1104 causes the processor 1102 to perform the method 100 in FIG. 2.

The processor 1102 may receive the digital model of the joint 3 and store the digital model in data store 1106, such as on RAM or a processor register. The digital model may be based on data received by the processor 1102, such a sensor data, medical imaging data, and 2D and 3D models, etc., from data memory 106, the communications port 1108, the input port 1011, and/or the user port 1110.

The processor 1102 is connected, via the user port 1110, to a display 1112 to show visual representations 1114 of the digital models. The processor 1102 may also send the digital models, and the calculated multiple angular distance values, as output signals via communication port 1108 to an output port 1012.

Although communications port 1108 and user port 1110 are shown as distinct entities, it is to be understood that any kind of data port may be used to receive data, such as a network connection, a memory interface, a pin of the chip package of processor 1102, or logical ports, such as IP sockets or parameters of functions stored on program memory 1104 and executed by processor 1102. These parameters may be stored on data memory 1106 and may be handled by-value or by-reference, that is, as a pointer, in the source code.

The processor 1102 may receive data through all these interfaces, which includes memory access of volatile memory, such as cache or RAM, or non-volatile memory, such as an optical disk drive, hard disk drive, storage server or cloud storage. The processing device 13 may further be implemented within a cloud computing environment, such as a managed group of interconnected servers hosting a dynamic number of virtual machines.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A computer-implemented method for estimating range of motion of a joint connecting a first bone to a second bone, the joint comprising a point of rotation defining rotation of the first bone relative to the second bone about the point of rotation, the method comprising:

generating a digital model of the joint, the digital model comprising:

a first mesh model representing the first bone and comprising a first set of mesh points; and a second mesh model representing the second bone and comprising a second set of mesh points;

determining polar coordinates for at least one of the first set of mesh points and the second set of mesh points, with the point of rotation as a pole of the polar coordinates;

calculating, based on the polar coordinates, multiple angular distance values relating to rotation of the joint, each of the multiple angular distance values being indicative of an angular distance between one point in the first set and one point in the second set, and the angular distance being indicative of the range of motion of the joint; and generating a visualization of the digital model, wherein a visual appearance of the first set of mesh points and the second set of mesh points is indicative of the angular distance value, wherein the visual appearance is a color value, and wherein the color value represents attainment, or failure to attain, a specified anatomic range of motion value.

2. The method of claim 1, wherein calculating the multiple angular distance values comprises selecting for a point in the first set, a point in the second set that is the nearest neighbor of the point in the first set based on the polar coordinates.

3. The method of claim 1, wherein the method comprises performing a nearest neighbor search.

4. The method of claim 3, wherein the nearest neighbor search is based on a space-partitioning data structure.

5. The method of claim 4, wherein the space-partitioning data structure comprises a k-d tree.

6. The method of claim 1, wherein the method comprises determining an angular distance value for multiple points on opposing surfaces of the first bone and the second bone.

7. The method of claim 1, wherein the angular distance value is a difference in an angle between the first set of mesh points and the second set of mesh points.

8. The method of claim 1, wherein the polar coordinates are two-dimensional comprising one distance value and one angle value.

9. The method of claim 1, wherein the polar coordinates are supplemented with an azimuthal angle to define spherical coordinates in three-dimensional space.

10. The method of claim 1, wherein the digital model of the joint comprises a digital model of an implant that replaces a part of at least one of the first bone, the second bone, or another implant, and defines the rotation of the first bone relative to the second bone.

11. The method of claim 10, wherein the method comprises:

receiving an update on the digital model of the implant; and re-calculating the multiple angular distance values based on the update.

12. The method of claim 11, wherein the update comprises position information of the implant.

13. The method of claim 12, wherein the update comprises a cut angle of the first bone or the second bone.

14. The method of claim 1, wherein at least one of the first mesh model and the second mesh model is a triangular mesh model defined by multiple triangles approximating a surface of the respective first bone and second bone.

15. The method of claim 14, wherein at least one of the first set of mesh points and the second set of mesh points comprise one or more of:

vertices of the triangles, and centroids of the triangles.

16. A computer system for estimating range of motion of a joint connecting a first bone to a second bone, the joint comprising a point of rotation defining rotation of the first bone relative to the second bone about the point of rotation, wherein the computer system comprises:

at least one processor configured to:

generate a digital model of the joint, the digital model comprising:

a first mesh model representing the first bone and comprising a first set of mesh points; and a second mesh model representing the second bone and comprising a second set of mesh points;

determine polar coordinates for at least one of the first set of mesh points and the second set of mesh points, with the point of rotation as a pole of the polar coordinates;

calculate, based on the polar coordinates, multiple angular distance values relating to rotation of the joint, each of the multiple angular distance values being indicative of an angular distance between one point in the first set and one point in the second set, and the angular distance being indicative of the range of motion of the joint; and generate a visualization of the digital model, wherein a visual appearance of the first set of mesh points and the second set of mesh points is indicative of the angular distance value, wherein the visual appearance is a color value, and wherein the color value represents attainment, or failure to attain, a specified anatomic range of motion value.

17. The computer system of claim 16, wherein the at least one processor is configured to:

select, for a point in the first set, a point in the second set that is the nearest neighbor of the point in the first set based on the polar coordinates.

18. The computer system of claim 16, wherein the at least one processor is configured to:

receive an update on the digital model of the implant; and re-calculating the multiple angular distance values based on the update.

* * * * *